United States Patent [19]
Hilfinger et al.

[11] Patent Number: 5,545,968
[45] Date of Patent: Aug. 13, 1996

[54] MOTOR-POWERED APPLIANCE FOR PERSONAL USE

[75] Inventors: Peter Hilfinger, Bad Homburg; Gerhard Kressner, Altenstadt; Michael Sauer, Bad Camberg, all of Germany

[73] Assignee: Braun Aktiengesellschaft, Frankfurter, Germany

[21] Appl. No.: 392,895

[22] PCT Filed: Sep. 3, 1993

[86] PCT No.: PCT/DE93/00805

§ 371 Date: May 4, 1995

§ 102(e) Date: May 4, 1995

[87] PCT Pub. No.: WO94/05228

PCT Pub. Date: Mar. 17, 1994

[30] Foreign Application Priority Data

Sep. 9, 1992 [DE] Germany .......................... 42 30 159.9

[51] Int. Cl.⁶ .................................................. H01M 10/42
[52] U.S. Cl. .................................................. 320/2
[58] Field of Search ...................... 320/2; 429/8

[56] References Cited

U.S. PATENT DOCUMENTS 5,138,245 8/1992 Mattinger et al. .......................... 320/2

FOREIGN PATENT DOCUMENTS

| 9004932 | 8/1990 | Germany | A61C 17/26 |
| 3937877C1 | 4/1991 | Germany | A61C 17/22 |
| 9101850 | 7/1992 | Germany | A61C 17/26 |

Primary Examiner—Peter S. Wong
Assistant Examiner—K. Shin
Attorney, Agent, or Firm—Fish & Richardson, P.C.

[57] ABSTRACT

The invention is directed to a motor-powered appliance 10 for personal use as, for example, an appliance for oral or dental hygiene, a shaver or the like, with a housing 12 for accommodating the drive means 20 as well as at least one rechargeable energy-storage cell 18. The housing 12 is composed of at least two housing sections 13, 14 sealingly connectible with each other. The appliance 10 has an associated case structure 22 incorporating in particular means 24 for charging the energy-storage cells 18, or in particular means 26 for the storage of attachments for the appliance 10. The case structure 22 includes two abutment means which, in forming an integral part of the case structure 22, provide a tool for severing the housing sections 13, 14.

16 Claims, 4 Drawing Sheets

MOTOR-POWERED APPLIANCE FOR PERSONAL USE

This invention relates to a motor-powered appliance for personal use as, for example, an appliance for oral or dental hygiene, a shaver or the like, with a housing for accommodating the drive means as well as at least one rechargeable energy-storage cell, with the housing being composed of at least two housing sections sealingly connectible with each other, and with the appliance having an associated case structure incorporating in particular means for charging the energy-storage cells, or in particular means for the storage of attachments for the appliance.

A motor-powered toothbrush of this type is already disclosed in applicant's DE 39 37 877 C1. The toothbrush disclosed therein is comprised of a two-part housing accommodating the function-related parts as, for example, an electric motor, a gear train, a drive shaft, at least one energy-storage cell, and an induction coil. To effect a tight seal between the two housing parts, these are snap-fitted or locked into engagement with each other. If the user wishes to open the toothbrush by disengaging the two housing parts for removing, for example, the spent energy-storage cell to dispose of it separately, this is practically not possible without the use of an additional tool, and only with difficulty where such an additional tool as a pliers, a saw or a knife is used.

When the two housing parts of an appliance are joined together by adhesive bonding or are welded together, opening of the appliance requires invariably the use of sharp-edged tools presenting, however, the risk of personal injury in particular to the average user who has no special skills in the handling of such tools.

Printed Specification DE 91 01 850 U1 discloses an electric toothbrush having a toothbrush housing of elliptical cross-section and a closure body detachably arranged at the end remote from the brush body. An annular groove is provided between the toothbrush housing and the closure body. To open the toothbrush housing, it is introduced into a cutout in a charging unit, such that a parting body projecting into the opening in the manner of a lug is received within the annular groove, followed by a rotating movement of the elliptical housing. This arrangement has the disadvantage that toothpaste residues or particles of dirt may deposit in the annular groove which, for one thing, may make it difficult to use the toothbrush in a hygienically safe manner and, for another thing, may obstruct the engaging action of the lug within the annular groove. Understanding the construction of the opening device and using it properly is difficult, in particular for the unskilled average user. The risk that the user decides against the use of the device to dispose of spent accumulators, for example, is accordingly high.

A case structure associated with the appliance and including means for charging the energy-storage cell or means for storing attachments for the appliance is already disclosed in applicant's patent application DE 37 31 587 A1 or the corresponding U.S. Pat. No. 5,033,617. This specification relates to a case serving essentially for the storage of tools of the oral and dental care type, in which the tools are protected from contamination from outside to the largest possible extent, while yet being readily identifiable and accessible for removal. This specification does not, however, suggest a case function that goes beyond the accommodation of attachments for the appliance or the charging of the energy-storage cell.

It is an object of the present invention to provide a user-friendly possibility of opening the appliance housing. This object is essentially accomplished in that the case structure includes two abutment means which, in forming an integral part of the case structure, provide a tool for severing the housing sections. The user is in a position to disengage the housing sections without major effort or without the need for additional tooling. Because the integral construction of the parting tool is accomplished by a modification of the case structure, the requirement of having to provide a separate additional tool which, under circumstances, may be misplaced or lost is obviated, presenting overall a low-cost solution. The risk of personal injury on opening of the housing is precluded in that the tool comprises merely two abutment means and has no sharp edges. The user is required to introduce one housing section of the appliance into the case structure using one hand, holding the case structure with the other hand, and then move the appliance in a swinging motion in the manner of a lever. In the process, the one housing section is located in position by the action of the abutment means, while the other housing section is allowed to follow the lever motion. After a specified lever force is exceeded, the two housing sections are disconnected, enabling the housing to be opened for the purpose of removing the energy-storage cell or also other components mounted in the housing.

Because the abutment means are disposed in offset relation to each other at a relative distance corresponding approximately to the axial length of one of the housing sections, a favorable lever action results requiring only little expenditure of force to sever the housing sections, so that any user is in a position to open the appliance when required without further help.

In a feature of the present invention, the abutment means are configured as a locating means and a stop means, the locating means ensuring a secure positioning of the appliance so that the lever action made possible by the stop means or the force therewith exerted on the housing sections enables the housing sections to be severed.

In a further feature of the present invention, a receiving opening and an inner wall of the receiving opening form the two abutment means. In this arrangement it is advantageous that the housing abuttingly engages the receiving opening and the inner wall of the receiving opening, so that in the subsequent lever motion performed by the housing, disconnection of the housing sections is accomplished.

Advantageously, the one abutment means is formed by a back panel of the case structure, while the second abutment means is formed by an intermediate bottom of the case structure. In this arrangement, the intermediate bottom of the case structure is conformed to the housing such as to enable the appliance to be located accurately. The back panel of the case structure provides the stop for the lever motion.

In a still further feature of the present invention, the back panel of the case structure includes a cutout, and the cutout and the housing have essentially like cross-sections of mating diameter. This configuration enables the appliance to be introduced into the case structure practically without clearance, thus simplifying disconnection of the housing sections.

In an embodiment of the present invention, the case structure includes a dome and a surface opposite the dome, with the dome providing the one abutment means and the opposite surface the second abutment means. In this arrangement, the dome serves the function of receiving and positioning the appliance, while the opposite surface acts as a stop means.

By providing the housing with a recess for receiving the dome and configuring the recess essentially such that its surface area is in abutting engagement with the dome, the appliance is prevented from becoming jammed or slipping out as use is made of the lever action.

In a further feature of the present invention, the surface opposite the dome is curved essentially cylindrically, and the housing of the appliance is preferably of a cylindrical configuration, with the curved surface as well as the housing having essentially like radii of curvature. This configuration enables the appliance to be in accurate abutting engagement with the curved surface, whereby disengagement of the housing sections is possible with a minimum of effort.

In a still further feature of the present invention, the two abutment means are formed by the receiving opening. When the housing is moved in the manner of a lever, this produces an elastic deformation of the wall of the case structure in which the receiving opening is provided, severing the housing sections.

In yet another feature of the present invention, the receiving opening has an inside diameter corresponding essentially to the outside diameter of the housing. This allows a nearly clearance-free arrangement of the housing in the receiving opening.

Advantageously, the receiving opening is preferably arranged in an end panel of the case structure. This embodiment affords particular ease of implementation from the manufacturing point of view, thus involving low cost.

A method of severing the housing sections of a motor-powered appliance for personal use is characterized by the following steps: Introducing one section of the housing into the case structure such that the housing section is arranged between the abutment means, holding the case structure with one of the user's hands and swinging the housing with the other of the user's hands in the manner of a lever, in which process the one housing section is located in position by the abutment means, while the other housing section follows the lever motion, causing the housing sections to be severed. By reason of the fact that the tool for parting the housing is integrally formed with the case structure and constituted by abutment means, the user is in a position to perform this parting action readily without the need for any additional tool.

In a greatly advantageous further feature of the present invention, both abutment means are provided on the dome. Parting of the housing sections can be accomplished in this further feature using a rotary motion of the housing, to which end the housing is seated on the dome. An additional swinging or lever motion of the housing is not necessary. This method of severing the housing sections can be applied with equal ease and effect to cylindrical housings as Well as housings of any desired cross-section including, for example, triangular or quadrangular cross-sections.

Advantageously, the one abutment means is provided by the dome while the second abutment means is provided by a lug-shaped protuberance arranged on one side of the dome. With the recess of the housing section which is approximately configured as a part mating with the dome including the lug-shaped protuberance, the housing is received by the dome substantially without clearance and in positive engagement therewith, whereby the complete housing is secured against radial displacement. When the housing is turned by the application of a force on the housing to sever the two housing sections, the positive abutting engagement between the housing section and the lug-shaped protuberance and the counterforce thereby produced secure the housing section in its position, effecting an easy disengagement of the two housing sections.

A further method of severing housing sections of a motor-powered appliance for personal use is characterized by the following steps: Manually seating the one section of the housing onto the case structure, such that the dome is received within the recess, holding the housing with one of the user's hands, while the user's other hand holds the case structure, and rotating the housing about a longitudinal center line. By rotating the housing, a locking engagement between the housing sections is canceled, disengaging the two housing sections, with the user being in a position to perform this parting operation readily for him- or herself.

Further features, advantages and application possibilities of the present invention will become apparent from the subsequent description of embodiments illustrated in more detail in the accompanying drawings. It will be understood that any single feature or any combination of single features described and/or represented by illustration form the subject-matter of the present invention, irrespective of their summarization in the claims and their back-references.

Figure 1:
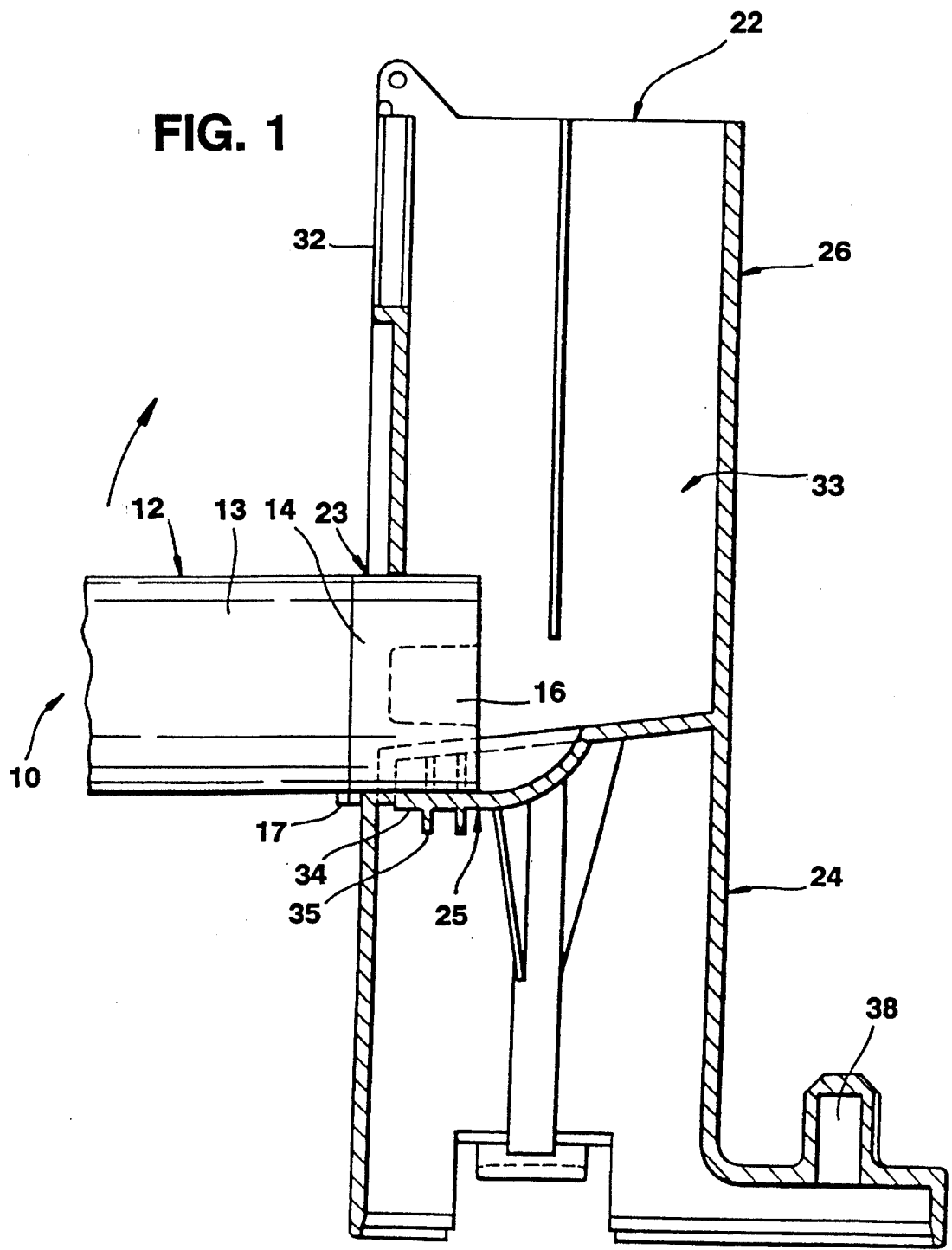
FIG. 1 is a view of a case structure (in section) illustrating a first embodiment of the present invention, showing a toothbrush (side view) introduced into a receiving opening.

Referring now to the Figures, there is shown a toothbrush 10 having a housing 12 and adapted to be powered by an electric motor 20 supplied with energy from energy-storage cells 18. By means of an induction coil 19, the energy-storage cells 18 are charged inductively when the toothbrush 10 is placed down on a dome 38 of a case structure 22 containing the charging means 24. A recess 16 in the housing 12 receives the dome 38.

Figure 2:
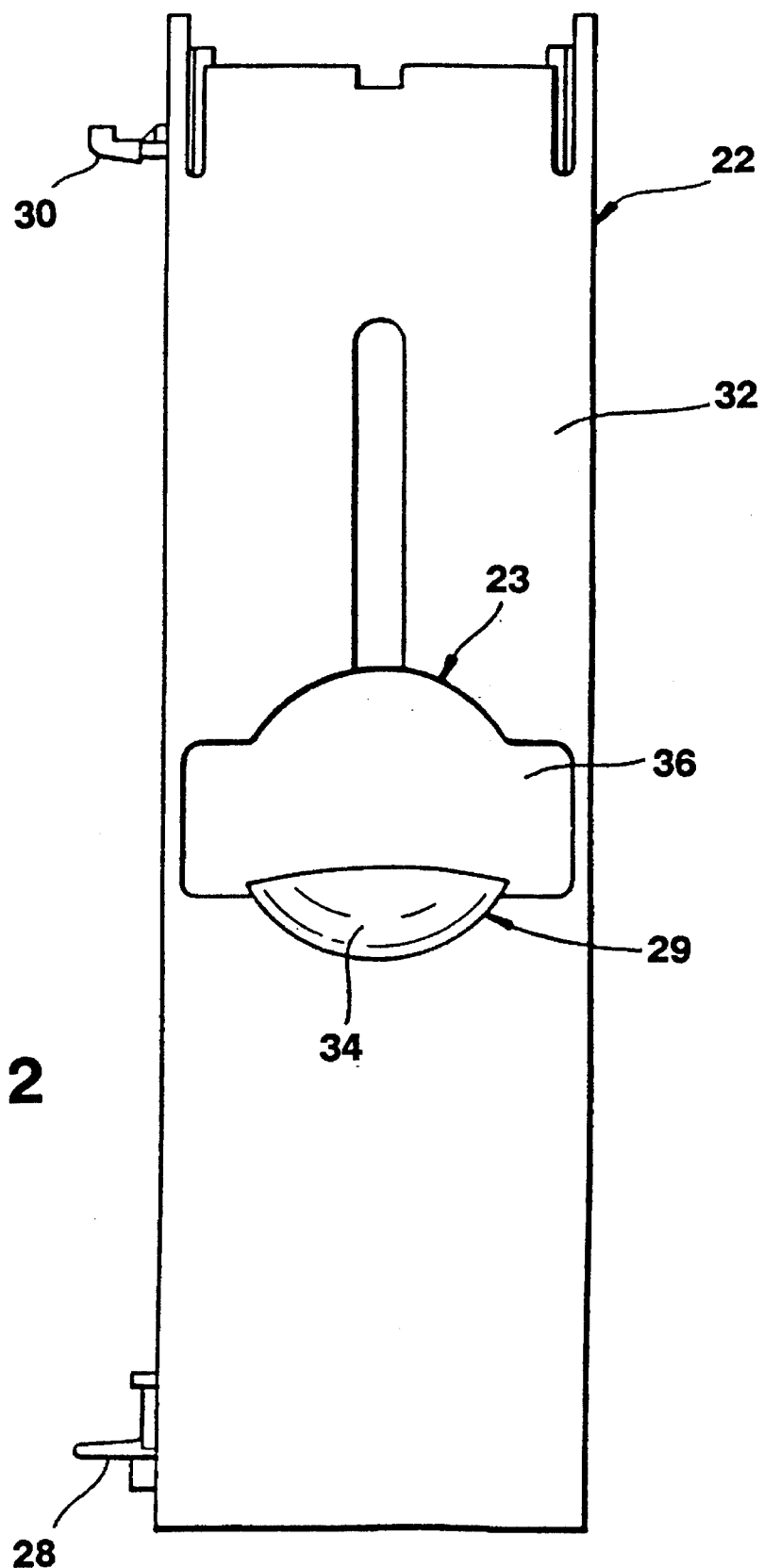
FIG. 2 is a view of the back panel Of the case structure of FIG. 1.

In addition, the case structure 22 of the first embodiment illustrated in FIGS. 1 and 2 has on its back panel 32 a receiving opening 23 configured as a cutout 36. The toothbrush 10 is partially inserted into this receiving opening 23. An inner wall 25 of the receiving opening 23, preferably an intermediate bottom 34, is configured such as to enable the housing section 14 of the appliance 10 to be held therein accurately. Stiffening means 35 formed on the underside of the intermediate bottom 34 increase the rigidity of the bottom configured as a locating means 29, that is, as one of the abutments for the parting operation.

To perform the parting operation, the housing section 14 of the housing 12 is inserted into the case structure 22 and arranged between the abutment means. In the process, the housing section comes to rest on the intermediate bottom 34. A retaining means 17 preferably disposed on either side of the parting line of the housing sections 13 and 14 serves as a stop for the housing section 14 to be inserted. The case structure 22 is then held with one hand, while the user's other hand grasps the housing section 13 of the toothbrush 10, moving it in the manner of a lever in the direction of the upper edge of the case structure 22 until the housing sections 13, 14 are severed. In this embodiment, the two abutment means are formed by the intermediate bottom 34 and by the upper edge of the receiving opening 23. Following severing of the housing sections 13 and 14, the energy-storage cells 18 located in the bottom part of the housing 12 can be withdrawn readily. It will be understood, of course, that once the housing 12 is open other components of the drive mechanism such as the motor, the gear train, printed circuit boards or other electrical or mechanical parts can be removed for disposal or replacement. Apart from the tool for severing the housing sections 13 and 14, the case structure 22 further includes in its upper area means 26 for storing toothbrush attachments and, in its lower area, means 24 for charging the energy-storage cells 18.

FIG. 2 shows the back panel 32 of the case structure 22 incorporating the receiving opening 23 for the housing 12. The cutout 36 corresponding to the receiving opening 23 is of an essentially cylindrical cross-section merging into the specially formed intermediate bottom 34 in its lower area. In this embodiment, the cutout 36 essentially conforming in cross-section to the housing 12 as well as the suitably formed intermediate bottom 34 enable the toothbrush 10 to be located and supported accurately for the parting operation. As an adapter, the case structure 22 includes a hook-shaped connecting member 30 as well as an electrical coupling means 28 providing a coupling for further appliances of the dental care type.

In a modification of the embodiment of FIGS. 1 and 2, it is possible to provide a circular receiving opening 23 for the housing 12 preferably in an end panel 33 of the case structure 22. To sever the housing sections 13, 14, housing section 14 of the housing 12 is introduced into the circular receiving opening 23 and then moved in the manner of a lever in the direction of the upper edge of the case structure 22. In this arrangement, the two abutment means are formed by circumferential segments of the receiving opening 23. The end panel 33 of the case structure 22 is elastically deformed, severing the housing sections 13, 14.

Figure 3:
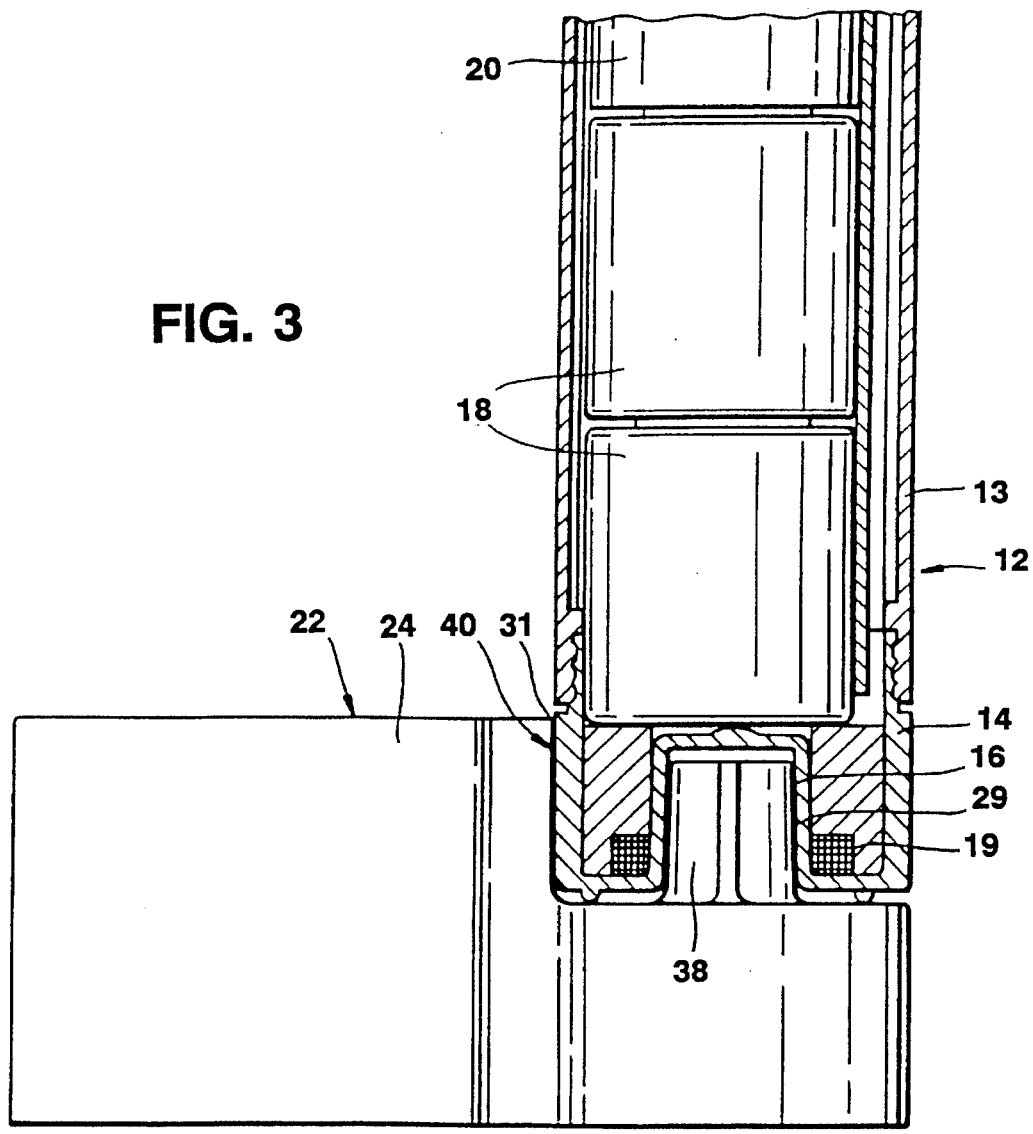
FIG. 3 is a view of a charging unit (side view) illustrating a second embodiment of the present invention, showing the toothbrush (in section) seated thereon.
Figure 4:
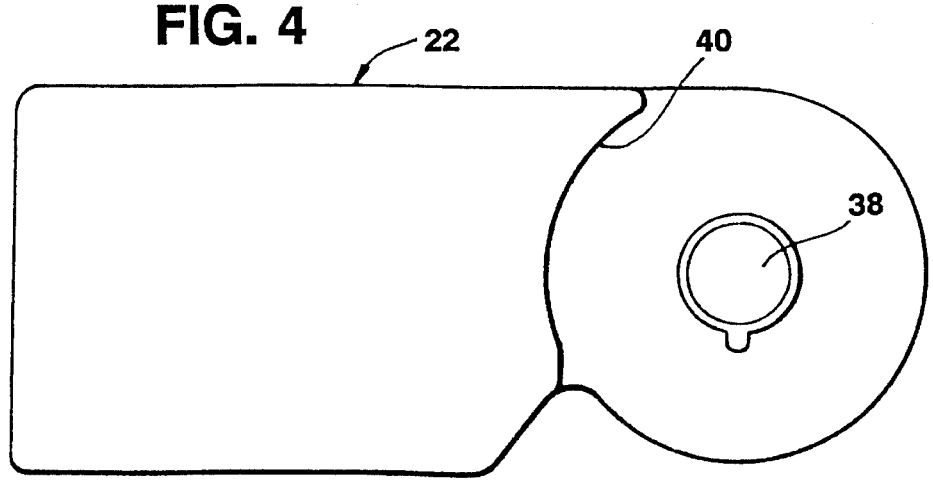
FIG. 4 is a top plan view of the charging unit of FIG. 3.

FIG. 3 illustrates a second embodiment of a case structure 22 incorporating the tool for severing the housing sections 13 and 14 as well as the means 24 for charging the energy-storage cells 18. In this embodiment, a dome 38 arranged on the case structure 22 is configured such that it is completely received within a recess 16 provided in the housing section 14 of the housing 12. Thus the dome serves first as a locating means 29 for the housing 12 and further as an abutment means during the parting operation of the housing sections 13 and 14. A surface 40 lying opposite the dome and providing the second abutment means is curved in such a fashion that its radius of curvature conforms to the housing 12 of the toothbrush 10. By virtue of this special configuration, the housing 12 rests with a surface area against the surface 40, with the parting line between the housing sections 13 and 14 being approximately flush with the upper edge of the surface 40. For the parting operation of the housing sections 13 and 14, the housing 12 is seated on the dome 38 as for recharging, with the surface areas of the dome 38 and the recess 16 having essentially interfitting engagement. While one hand holds the case structure 22 securely in place, the housing section 13 of the housing 12 is urged against the upper edge of the surface 40 providing the stop means 31 in the manner of a lever, until the housing sections 13, 14 are severed. Following severing, the housing 12 can be opened, enabling the user to remove the energy-storage cells 18 readily for separate disposal.

Figure 5:
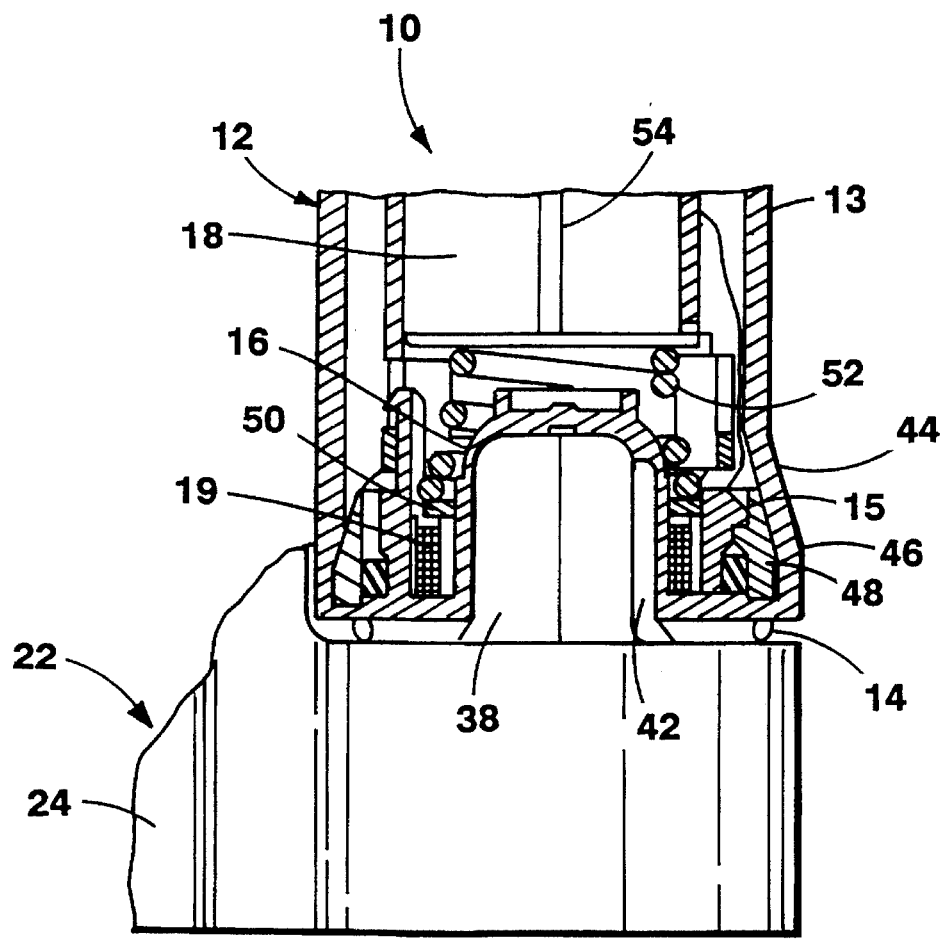
FIG. 5 is a view of a portion of a charging unit (side view) illustrating a third embodiment of the present invention, showing the toothbrush (in section) seated thereon.

FIG. 5 illustrates a third embodiment of a case structure 22 with toothbrush 10. In addition to incorporating the tool for severing the housing sections 13 and 14, the case structure 22 also includes the means 24 necessary for recharging the appliance. A dome 38 arranged on the case structure 22 includes a lug-shaped protuberance 42 extending nearly along the full height of the dome. A recess 16 provided in the housing section 14 is configured as a part mating with the dome 38 including its lug-shaped protuberance 42. The dome 38 with its lug-shaped protuberance 42 is practically fully received within the recess 16 when the housing 12 is seated on the case structure 22. The dome 38 thus serves the function of radially securing the housing 12 in position, thus providing a first abutment means. By turning the housing 12 about a longitudinal center line 54 for disengagement of the two housing sections 13 and 14, a force is exerted on the housing section 14, causing the lug-shaped protuberance 42 to act as a second abutment means. Owing to its positive abutting engagement with the recess 16, the lug-shaped protuberance 42 prevents the housing section 14 from following this turning motion, thus enabling the two housing sections 13 and 14 to be severed. In the parting operation, a locking engagement between the housing section 13 and the housing section 14 is canceled. This locking engagement is produced by reason of the fact that projections 15 provided on the housing section 14 engage with projections 46 of a bayonet ring 44 fixedly connected to the housing section 13, snapping into a locked position between extensions provided on either side of the projections 46. A spring 52 is provided between an energy-storage cell 18 inductively charged by means of an induction coil 19 and a washer 50 arranged on the housing section 14. This spring 52 supports the energy-storage cells 18 in the housing 12 in a secure and clearance-free manner as long as the two housing sections 13 and 14 are fixedly connected to each other, with a ring seal 48 preventing the ingress of humidity between the housing sections 13 and 14. During the parting operation of the two housing sections 13 and 14, when the locking engagement between the housing sections 13 and 14 is overtraveled by turning the housing section 13, the tension of the spring 52 will be released, the spring force then acting to disengage the housing sections 13 and 14. This then allows the removal of the energy-storage cells 18 and any further components mounted in the housing 12.

We claim:

1. A motor-powered appliance for personal use (10) as, for example, an appliance for oral or dental hygiene, a shaver or the like, with a housing (12) for accommodating the drive means (20) as well as at least one rechargeable energy-storage cell (18), with the housing (12) comprising at least two housing sections (13, 14) sealingly connectible with each other, and with the appliance (10) having an associated case structure (22) incorporating in particular means (24) for charging the energy-storage cells (18), or in particular means (26) for the storage of attachments for the appliance (10), characterized in that the case structure (22) includes in particular two abutment means which, in forming an integral part of the case structure (22), provide a tool for severing the housing sections (13, 14).

2. The motor-powered appliance for personal use as claimed in claim 1, characterized in that the abutment means are disposed in offset relation to each other at a relative distance corresponding approximately to the axial length of one of the housing sections (13, 14).

3. The motor-powered appliance for personal use as claimed in claim 1 or claim 2, characterized in that the abutment means are configured as a locating means (29) and a stop means (31).

4. The motor-powered appliance for personal use as claimed in claim 1, characterized in that a receiving opening (23) and an inner wall (25) of the receiving opening (23) form the two abutment means.

5. The motor-powered appliance for personal use as claimed in claim 1, characterized in that the one abutment means is formed by a back panel (32) of the case structure (22), while the second abutment means is formed by an intermediate bottom (34) of the case structure (22).

6. The motor-powered appliance for personal use as claimed in any claim 1, characterized in that a back panel (32) of the case structure (22) includes a cutout (36), and that the cutout (36) and the housing (12) have essentially like cross-sections of mating diameter.

7. The motor-powered appliance for personal use as claimed in claim 1, characterized in that the case structure (22) includes a dome (38) and a surface (40) opposite the dome (38), and that the dome (38) provides the one abutment means and the opposite surface (40) the second abutment means.

8. The motor-powered appliance for personal use as claimed in claim 7, characterized in that the housing (12) is provided with a recess (16) for receiving the dome (38), and that the recess (16) is essentially configured such that its surface area is in abutting engagement with the dome (38).

9. The motor-powered appliance for personal use as claimed in claim 7 or claim 8, characterized in that the surface (40) opposite the dome (38) is curved essentially cylindrically and the housing (12) is preferably of a cylindrical configuration, and that the curved surface (40) and the housing (12) have essentially like radii of curvature.

10. The motor-powered appliance for personal use as claimed in claim 1, characterized in that the two abutment means are formed by the receiving opening (23).

11. The motor-powered appliance for personal use as claimed in claim 10, characterized in that the receiving opening (23) has an inside diameter corresponding essentially to the outside diameter of the housing (12).

12. The motor-powered appliance for personal use as claimed in claim 10 or claim 11, characterized in that the receiving opening (23) is preferably arranged in an end panel (33) of the case structure (22).

13. A method of severing housing sections of a motor-powered appliance for personal use, in particular as claimed in claim 1, characterized in that it involves the following steps:

1. Introducing one section (14) of the housing (12) into the case structure (22) such that the housing section (14) is arranged between the abutment means;

2. holding the case structure (22) with the one of the user's hands; and 3. swinging the housing (12) with the other of the user's hands in the manner of a lever, in which process the housing section (14) is located in position by the abutment means.

14. The motor-powered appliance for personal use as claimed in claim 1, characterized in that both abutment means are provided on the dome (38).

15. The motor-powered appliance for personal use as claimed in claim 14, characterized in that the one abutment means is provided by the dome (38) while the second abutment means is provided by a lug-shaped protuberance (42) arranged on one side of the dome (38).

16. A method of severing housing sections of a motor-powered appliance for personal use, in particular as claimed in any one of the claims 14 or 15, characterized in that it involves the following steps:

1. Manually seating one section (14) of the housing (12) onto the case structure (22), such that the dome (38) is received within a recess provided on the housing (12);

2. holding the housing (12) with one of the user's hands, while the user's other hand holds the case structure (22); and 3. rotating the housing (12) about a longitudinal center line (54).

* * * * *